United States Patent [19]

Carr et al.

[11] 4,254,129
[45] Mar. 3, 1981

[54] PIPERIDINE DERIVATIVES

[75] Inventors: Albert A. Carr; Joseph E. Dolfini, both of Cincinnati, Ohio; George J. Wright, Richmond, Va.

[73] Assignee: Richardson-Merrell Inc., Wilton, Conn.

[21] Appl. No.: 28,813

[22] Filed: Apr. 10, 1979

[51] Int. Cl.³ .................. C07D 211/34; A61K 31/445
[52] U.S. Cl. .................................. 424/267; 546/239; 546/240
[58] Field of Search ................. 546/239, 240; 424/267

[56] References Cited

U.S. PATENT DOCUMENTS

| | | | |
|---|---|---|---|
| 3,687,956 | 8/1972 | Zivkovic | 546/240 |
| 3,806,526 | 4/1974 | Carr et al. | 546/237 |
| 3,829,433 | 8/1974 | Carr et al. | 546/237 |
| 3,862,173 | 1/1975 | Carr et al. | 546/237 |
| 3,878,217 | 4/1975 | Carr et al. | 546/237 |
| 3,922,276 | 11/1975 | Duncan et al. | 546/237 |
| 3,931,197 | 1/1976 | Carr et al. | 546/237 |
| 3,941,795 | 3/1976 | Carr et al. | 546/237 |
| 3,946,022 | 3/1976 | Carr et al. | 546/237 |
| 3,956,296 | 5/1976 | Duncan et al. | 546/237 |
| 3,965,257 | 6/1976 | Carr et al. | 546/237 |

Primary Examiner—Norma S. Milestone
Attorney, Agent, or Firm—John J. Kolano; George W. Rauchfuss, Jr.; Salvatore R. Conte

[57] ABSTRACT

Novel compounds of the following formula:

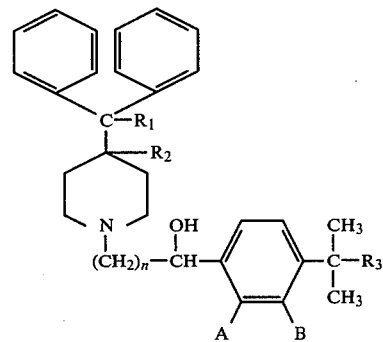

wherein $R_1$ is hydrogen or hydroxy; $R_2$ is hydrogen; or $R_1$ and $R_2$ taken together form a second bond between the carbon atoms bearing $R_1$ and $R_2$; n is an integer of from 1 to 5; $R_3$ is —$CH_3$, —$CH_2OH$, —COOH or —COOalkyl wherein the alkyl moiety has from 1 to 6 carbon atoms and is straight or branched; and each of A and B is hydrogen or hydroxy; with the provisos that at least one of A or B is hydrogen and one of A or B is other than hydrogen when $R_3$ is —$CH_3$; and pharmaceutically acceptable salts thereof.

11 Claims, No Drawings

PIPERIDINE DERIVATIVES

FIELD OF INVENTION

This invention relates to novel substituted piperidine derivatives. More particularly, this invention relates to substituted phenyl 4-substituted piperidinoalkanol derivatives which are useful as antihistamines, antiallergy agents and bronchodilators and to methods of making and using the same.

BACKGROUND OF INVENTION

Related piperidine derivatives having antihistamine properties are disclosed in the following U.S. patents which are the only material and pertinent references known to applicants:

U.S. Pat. No. 3,806,526 issued Apr. 23, 1974,
U.S. Pat. No. 3,829,433 issued Aug. 13, 1974,
U.S. Pat. No. 3,862,173 issued Jan. 21, 1975,
U.S. Pat. No. 3,878,217 issued Apr. 15, 1975,
U.S. Pat. No. 3,931,197 issued Jan. 6, 1976,
U.S. Pat. No. 3,941,795 issued Mar. 2, 1976,
U.S. Pat. No. 3,946,022 issued Mar. 23, 1976, and
U.S. Pat. No. 3,965,257 issued June 22, 1976.

SUMMARY OF INVENTION

The novel substituted piperidine derivatives of this invention useful as antihistamines, antiallergy agents, and bronchodilators are represented by the formula

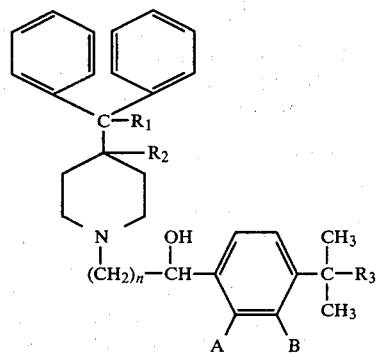

Formula I wherein $R_1$ represents hydrogen or hydroxy; $R_2$ represents hydrogen; or $R_1$ and $R_2$ taken together form a second bond between the carbon atoms bearing $R_1$ $R_2$; n is an integer of from 1 to 5; $R_3$ is —$CH_3$, —$CH_2OH$, —COOH or —COOalkyl wherein the alkyl moiety has from 1 to 6 carbon atoms and is straight or branched; A and B are individually hydrogen or hydroxy; with the provisos that at least one of A or B is hydrogen, and one of A or B is other than hydrogen when $R_3$ is —$CH_3$; and pharmaceutically acceptable salts and individual optical isomers thereof.

DETAILED DESCRIPTION OF INVENTION

It can be seen from the above Formula I that compounds of this invention are 4-diphenylmethylpiperidine derivatives as represented by the following Formula II, 4-(hydroxydiphenylmethyl)piperidine derivatives as represented by the following Formula III, or 4-diphenylmethylenepiperidine derivatives as represented by the following Formula IV:

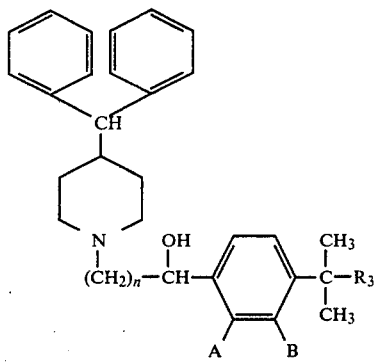

Formula II

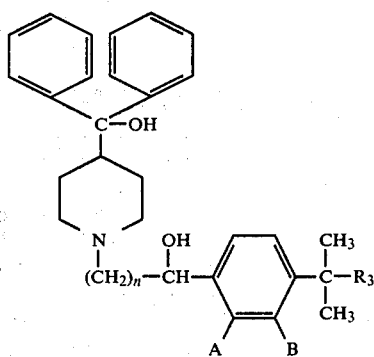

Formula III

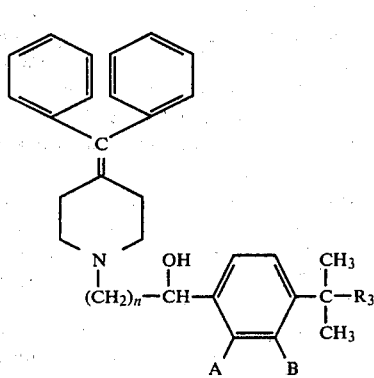

Formula IV

In the above Formulas II, III and IV the various symbols n, $R_3$, A and B have the meanings defined in Formula I.

Illustrative examples of straight or branched alkyl groups having from 1 to 6 carbon atoms as referred to herein are methyl, ethyl, n-propyl, isopropyl, n-butyl, sec-butyl, tert-butyl, n-pentyl, neopentyl and n-hexyl.

Preferred compounds of this invention are those of general Formulas III and IV wherein n, $R_3$, A and B have the meanings defined hereinbefore, and may be represented by the following Formula V.

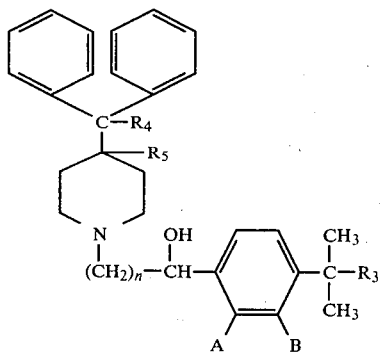

Formula V

In the above Formula V, R₄ represents hydroxy and R₅ represents hydrogen, or R₄ and R₅ taken together form a second bond between the carbon atoms bearing R₄ and R₅; and n, R₃, A and B have the meanings defined in general Formula I.

More preferred compounds of this invention are those of general Formula V wherein n is the integer 3 and B is hydrogen, and of these compounds those wherein R₃ is —COOH are most preferred.

This invention also includes pharmaceutically acceptable salts of the compounds of the hereinbefore set forth formulas. Pharmaceutically acceptable acid addition salts of the compounds of this invention are those of any suitable inorganic or organic acid. Suitable inorganic acids are, for example, hydrochloric, hydrobromic, sulfuric, and phosphoric acids. Suitable organic acids include carboxylic acids, such as, acetic, propionic, glycolic, lactic, pyruvic, malonic, succinic, fumaric, malic, tartaric, citric, cyclamic, ascorbic, maleic, hydroxymaleic, and dihydroxymaleic, benzoic, phenylacetic, 4-aminobenzoic, 4-hydroxybenzoic, anthranillic, cinnamic, salicyclic, 4-aminosalicyclic, 2-phenoxybenzoic, 2-acetoxybenzoic, and mandelic acid, sulfonic acids, such as, methanesulfonic, ethanesulfonic and β-hydroxyethanesulfonic acid. Non-toxic salts of the compounds of the above-identified formulas formed with inorganic or organic bases are also included within the scope of this invention and include, for example, those of alkali metals, such as, sodium, potassium and lithium, alkaline earth metals, for example, calcium and magnesium, light metals of group IIIA, for example, aluminum, organic amines, such as, primary, secondary or tertiary amines, for example, cyclohexylamine, ethylamine, pyridine, methylaminoethanol and piperazine. The salts are prepared by conventional means as, for example, by treating a compound of Formula I with an appropriate acid or base.

Illustrative examples of compounds of this invention are the following:

4-[4-[4-(hydroxydiphenylmethyl)-1-piperidinyl]-1-hydroxybutyl]-α,α-dimethylbenzeneacetic acid, 4-[4-[4-(diphenylmethyl)-1-piperidinyl]-1-hydroxybutyl]-α,α-dimethylbenzeneacetic acid, 4-[4-[4-(diphenylmethyl)-1-piperidinyl]-1-hydroxybutyl]-α,α-dimethylbenzeneacetic acid, 4-[4-[4-(diphenylmethylene)-1-piperidinyl]-1-hydroxybutyl]-α,α-dimethylbenzeneacetic acid, 4-[4-[4-(hydroxydiphenylmethyl)-1-piperidinyl]-1-hydroxybutyl]-α,α-dimethyl-3-hydroxybenzene acetic acid, 4-[4-[4-(hydroxydiphenylmethyl)-1-piperidinyl]-1-hydroxybutyl]-α,α-dimethyl-2-hydroxybenzene acetic acid, 4-[4-[4-(diphenylmethylene-1-piperidinyl]-1-hydroxybutyl]-α,α-dimethyl-3-hydroxybenzene acetic acid, 5-[4-[4-(diphenylmethylene)-1-piperidinyl]-1-hydroxypentyl]-α,α-dimethylbenzeneacetic acid, 3-[4-[4-(hydroxydiphenylmethyl)-1-piperidinyl]-1-hydroxypropyl]-α,α-dimethylbenzeneacetic acid, 2-[4-[4-(hydroxydiphenylmethyl)-1-piperidinyl]-1-hydroxyethyl]-α,α-dimethylbenzeneacetic acid, ethyl 4-[4-[4-(hydroxydiphenylmethyl)-1-piperidinyl]-1-hydroxybutyl]-α,α-dimethylbenzeneacetate, n-pentyl 4-[4-[4-(diphenylmethyl)-1-piperidinyl]-1-hydroxybutyl]-α,α-dimethylbenzeneacetate, ethyl 4-[4-[4-(diphenylmethylene)-1-piperidinyl]-1-hydroxybutyl]-α,α-dimethylbenzeneacetate, methyl 4-[4-[4-(hydroxydiphenylmethyl)-1-piperidinyl]-1-hydroxybutyl]-α,α-dimethylbenzeneacetate, ethyl 4-[4-[4-(hydroxydiphenylmethyl)-1-piperidinyl]-1-hydroxybutyl]-α,α-dimethyl-(3-hydroxybenzene)acetate, n-propyl 4-[4-[4-(hydroxydiphenylmethyl)-1-piperidinyl]-1-hydroxybutyl]-α,α-dimethyl-(2-hydroxybenzene)acetate, n-hexyl 4-[4-[4-(diphenylmethylene)-1-piperidinyl]-1-hydroxybutyl]-α,α-dimethyl-(3-hydroxybenzene)acetate, ethyl 5-[4-[4-(diphenylmethylene)-1-piperidinyl]-1-hydroxypentyl]-α,α-dimethylbenzeneacetate, α,α-diphenyl-1-(4-(4-tert-butyl-2-hydroxy)phenyl)-4-hydroxybutyl-4-piperidinemethanol, α,α-diphenyl-1-(4-(4-tert-butyl-3-hydroxy)phenyl)-4-hydroxybutyl-4-piperidinemethanol, α,α-diphenyl-1-(3-(4-tert-butyl-2-hydroxy)phenyl)-3-hydroxypropyl-4-piperidinemethanol, α,α-diphenyl-1-(5-(4-tert-butyl-2-acetyloxy)phenyl)-5-hydroxypentyl-4-piperidinemethanol, α,α-diphenyl-1-(4-(4-hydroxy-tert-butyl-2-hydroxy)phenyl)-4-hydroxybutyl-4-piperidinemethanol, α,α-diphenyl-1-(4-(4-hydroxy-tert-butyl-3-hydroxy)phenyl)-4-hydroxybutyl-4-piperidinemethanol, α,α-diphenyl-1-(3-(4-hydroxy-tert-butyl-2-hydroxy)phenyl)-3-hydroxypropyl-4-piperidinemethanol, α,α-diphenyl-1-(4-(4-hydroxy-tert-butyl)phenyl-4-hydroxybutyl-4-piperidinemethanol, 1-(4-tert-butyl-2-hydroxyphenyl)-4-(4-(diphenylmethylene)-1-piperidinyl)butanol, 1-(4-tert-butyl-3-hydroxyphenyl)-4-(4-(diphenylmethylene)-1-piperidinyl)butanol, 1-(4-tert-butyl-3-hydroxyphenyl)-2-(4-(diphenylmethylene)-1-piperidinyl)ethanol, 1-(4-tert-butyl-2-butyryloxyphenyl)-6-(4-(diphenylmethyl)-1-piperidinyl)hexanol, (1-(4-hydroxy-tert-butyl-2-hydroxyphenyl)-4-(4-diphenylmethylene)-1-piperidinyl)butanol, 1-(4-hydroxy-tert-butyl-3-hydroxyphenyl)-4-(4-(diphenylmethylene)-1-piperidinyl)butanol, 1-(4-hydroxy-tert-butyl-3-hydroxyphenyl)-2-(4-diphenylmethylene)-1-piperidinyl)ethanol, 1-(4-hydroxy-tert-butylphenyl)-4-(4-(diphenylmethylene)-1-piperidinyl)butanol, 1-(4-hydroxy-tert-butylphenyl)-3-(4-diphenylmethyl)-1-piperidinyl)propanol, tert-butyl 2-[4-[4-(hydroxydiphenylmethyl)-1-piperidinyl]-1-hydroxyethyl]-α,α-dimethylbenzeneacetate.

The compounds of this invention are useful as antihistamines, antiallergy agents and bronchodilators and may be administered alone or with suitable pharmaceutical carriers, and can be in solid or liquid form such as, tablets, capsules, powders, solutions, suspensions or emulsions.

The compounds of this invention can be administered orally, parenterally, for example, subcutaneously, intravenously, intramuscularly, intraperitoneally, by intranasal instillation or by application to mucous membranes, such as, that of the nose, throat and bronchial tubes, for example, in an aerosol spray containing small particles of a compound of this invention in a spray or dry powder form.

The quantity of novel compound administered will vary depending on the patient and the mode of administration and can be any effective amount. The quantity of novel compound administered may vary over a wide range to provide in a unit dosage an effective amount of from about 0.01 to 20 mg/kg of body weight of the patient per day to achieve the desired effect. For example, the desired antihistamine, antiallergy and bronchodilator effects can be obtained by consumption of a unit dosage form such as a tablet containing 1 to 50 mg of a novel compound of this invention taken 1 to 4 times daily.

The solid unit dosage forms can be of the conventional type. Thus, the solid form can be a capsule which can be the ordinary gelatin type containing a novel compound of this invention and a carrier, for example, lubricants and inert fillers such as lactose, sucrose or cornstarch. In another embodiment the novel compounds are tableted with conventional tablet bases such as lactose, sucrose or cornstarch in combination with binders such as acacia, cornstarch or gelatin, disintegrating agents such as cornstarch, potato starch or alginic acid, and a lubricant such as stearic acid or magnesium stearate.

The compounds of this invention may also be administered in injectable dosages by solution or suspension of the compounds in a physiologically acceptable diluent with a pharmaceutical carrier which can be a sterile liquid such as water and oils, with or without the addition of a surfactant and other pharmaceutically acceptable adjuvants. Illustrative of oils there can be mentioned those of petroleum, animal, vegetable or synthetic origin, for example, peanut oil, soybean oil or mineral oil. In general, water, saline, aqueous dextrose and related sugar solution and glycols such as propylene glycol or polyethylene glycol are preferred liquid carriers, particularly for injectable solutions.

For use as aerosols the compounds of this invention in solution or suspension may be packaged in a pressurized aerosol container together with suitable propellants, for example, hydrocarbon propellants such as, propane, butane or isobutane with the usual adjuvants as may be necessary or desirable. The compounds also may be administered in a non-pressurized form such as in a nebulizer or atomizer.

The term patient as used herein is taken to mean warm blooded animals, birds, mammals, for example, humans cats, dogs, horses, sheep, bovine cows, pigs, lambs, rats, mice and guinea pigs.

To demonstrate the utility of the compounds of this invention 4-[4-[4-(hydroxydiphenylmethyl)-1-piperidinyl]-1-hydroxybutyl]-$\alpha,\alpha$-dimethylbenzeneacetic acid at a concentration of $1 \times 10^{-7}$ M gives a significant reduction in histamine induced isolated guinea pig ileal muscle contraction.

The compounds of this invention are prepared by various means, and certain compounds of the invention are employed to prepare other compounds of the invention as will become apparent by the following.

It will be apparent from the following that the compounds of Formula I except those wherein B is OH may be prepared in one step by reduction of the corresponding ketone or in two steps by reduction of an appropriate ketone followed by base hydrolysis depending on the compound desired and the reducing reagent employed as illustrated by the following flow charts.

Scheme I

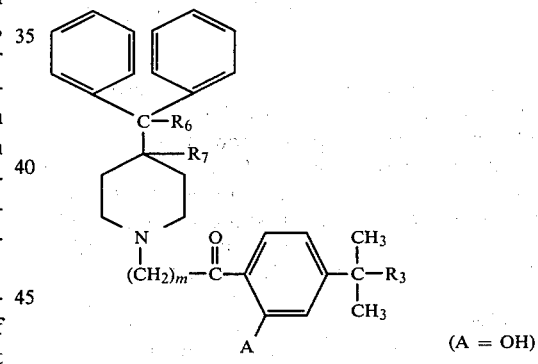

(I)

(A = OH)

LiAlH$_4$, B$_2$H$_6$, NaBH$_4$, KBH$_4$, or catalytic reduction

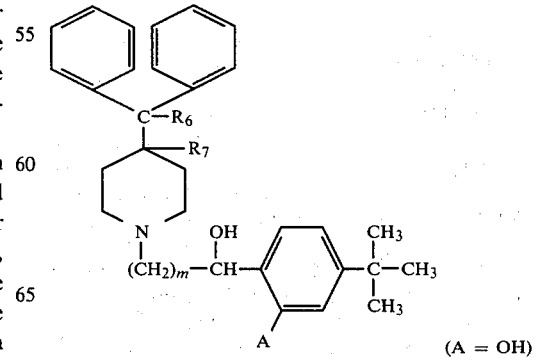

(VII)

(A = OH)

Scheme II

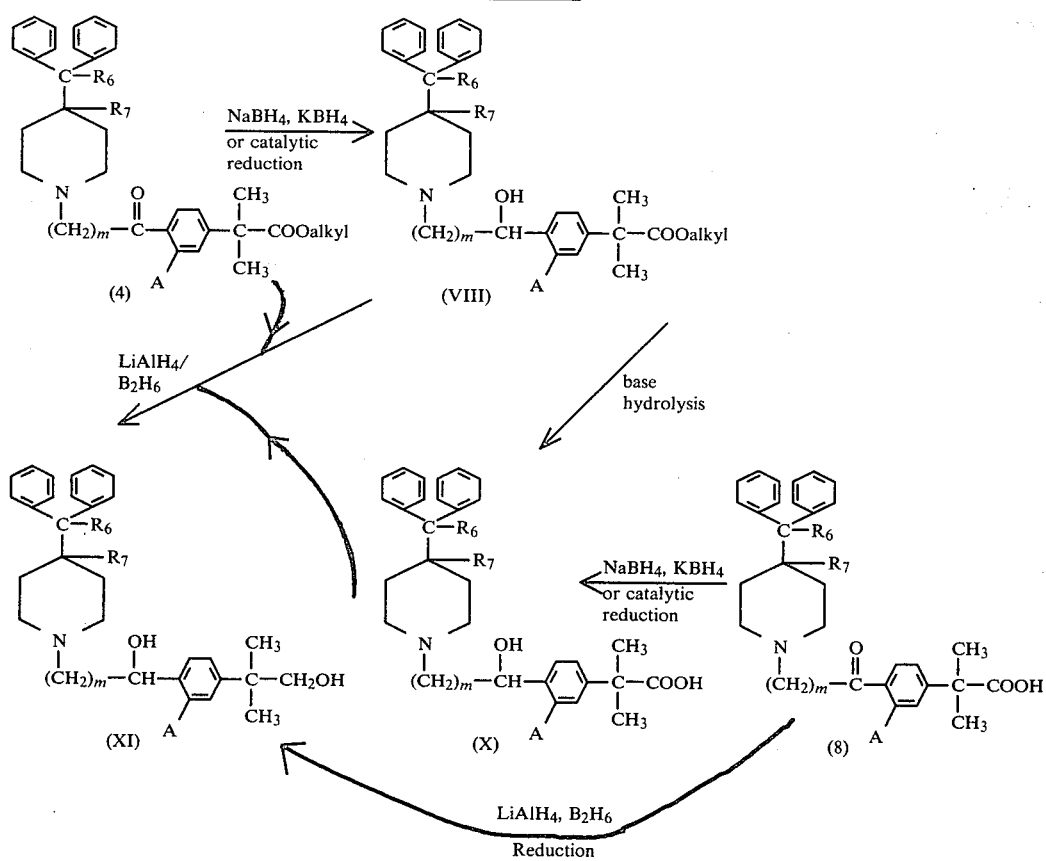

In the above Schemes I and II R$_6$ is hydrogen or hydroxy; R$_7$ is hydrogen; or R$_6$ and R$_7$ together form a second bond between the carbon atoms bearing R$_6$ and R$_7$; m is an integer of from 1 to 5; A is hydrogen or hydroxy; and alkyl in compounds (4) and (VIII) has from 1 to 6 carbon atoms and is straight or branched.

Reduction of the various compounds illustrated in Schemes I and II using, for example, sodium borohydride or potassium borohydride is carried out in lower alcohol solvents, such as, methanol, ethanol, isopropyl alcohol or n-butanol. When lithium aluminum hydride or diborane are used as reducing agents as illustrated in Schemes I and II suitable solvents are ethers, for example, diethyl ether, tetrahydrofuran or dioxane. These reduction reactions are carried out at temperatures ranging from about 0° C. to the reflux temperature of the solvent, and the reaction time varies from about 0.5 to 8 hours.

Catalytic reduction may also be employed in the preparation of compounds of the invention as shown in Schemes I and II above, using, for example, Raney nickel, palladium, platinum or rhodium catalysts in lower alcohol solvents, such as, methanol, ethanol, isopropyl alcohol or n-butanol or acetic acid or their aqueous mixtures, or by the use of aluminum isopropoxide in isopropyl alcohol. Reduction using sodium borohydride is preferred over catalytic reduction in preparing, for example, compounds, (VIII) or (X). When in compounds (1), (4) and (8), R$_6$ and R$_7$ form a double bond, catalytic reduction is less preferred. In preparing the alcohols represented by compounds (XI) lithium aluminum hydride is the preferred reducing agent when the starting material employed is either compounds (4) or (VIII) and diborane is preferred when the starting material is compounds (X) or (8). Base hydrolysis of compounds (VIII) to give compounds (X) is achieved by procedures well known in the art, for example, by treatment with an inorganic base, such as, sodium hydroxide or potassium hydroxide in an aqueous lower alcoholic solvent, such as, aqueous methanol, ethanol, isopropyl alcohol or n-butanol at reflux temperatures for about ½ hour to 12 hours.

The compounds of Formula I wherein B is hydroxy and R$_3$ is —CH$_3$ or —COOH are prepared by treating a compound of the following Formula XII with a slight excess of thallium trifluoroacetate in trifluoroacetic acid at reflux temperature (about 72° C.) for about three hours after which 1 equivalent of lead tetraacetate in trifluoroacetic acid is added. The mixture is stirred for about ½ hour then 1 equivalent of triphenylphosphine is added. Stirring is continued for about ½ hour followed by removal of excess solvent at reduced pressure then the addition of cold and dilute (6 N) hydrochloric acid. The lead chloride and thallium chloride are filtered off, and the filtrate is made alkaline with 10% sodium hydroxide solution and a minimum amount of ethanol is added to bring about complete solution. The solution is refluxed for about 4 hours, neutralized, then concentrated, extracted with toluene, dried, filtered and concentrated to give the appropriate compound of Formula I wherein R$_3$ is methyl or —COOH and B is hydroxy. The compounds of Formula I wherein R$_3$ is —COOalkyl and B is hydroxy are obtained by treating 1 equivalent of the corresponding derivative wherein $R_3$ is —COOH with 2 or 3 equivalents of boron trifluoride etherate and about 20 or 30 equivalents of an alcohol of the formula $R_8OH$ wherein $R_8$ is a straight or branched alkyl group having from 1 to 6 carbon atoms. The mixture is refluxed for about 24 hours, according to the general procedure of Kadaba, J. Pharm. Sci. 63, 1333 (1974). Upon cooling the mixture is added to about 100 ml of water, concentrated at reduced pressure on a water bath, and the product purified by crystallization from alcohols or mixtures thereof with toluene.

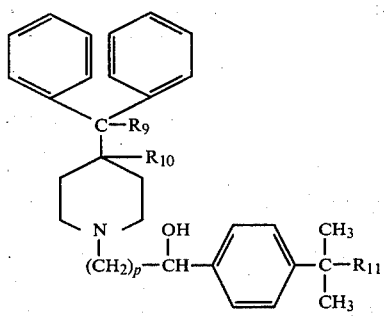

Formula XII

In the above Formula XII, $R_9$ is hydrogen or trifluoroacetyloxy; $R_{10}$ is hydrogen; or $R_9$ and $R_{10}$ taken together form a second bond between the carbon atoms bearing $R_9$ and $R_{10}$; p is an integer of from 1 to 5; and $R_{11}$ is methyl or —COOalkyl wherein the alkyl moiety has from 1 to 6 carbon atoms and is straight or branched.

The compounds of Formula XII wherein $R_{11}$ is methyl and each of $R_9$ and $R_{10}$ is hydrogen or $R_9$ and $R_{10}$ taken together form a second bond between the carbon atoms bearing $R_9$ and $R_{10}$ are known in the art or may be prepared by procedures well known in the art. The compounds of Formula XII wherein each of $R_9$ and $R_{10}$ is hydrogen or $R_9$ and $R_{10}$ taken together form a second bond between the carbon atoms bearing $R_9$ and $R_{10}$ and $R_{11}$ is —COOalkyl are prepared as described herein. See compounds VIII in Scheme II. The compounds of Formula XII wherein $R_9$ is trifluoroacetyloxy are prepared by treating a ketone of the Formula

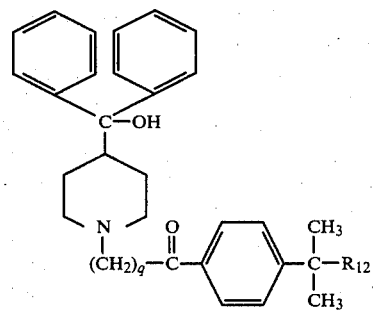

Formula XIII wherein $R_{12}$ is methyl or —COOalkyl, and q is an integer of from 1 to 5; with trifluoroacetic anhydride for about 2 to 6 hours at temperatures of about 0° to 25° C. with stirring followed by catalytic reduction using, for example, platinum oxide in methanol and 1 atmosphere hydrogen in a Paar apparatus to take up an equivalent amount of hydrogen.

The ketone compounds used herein as starting materials, i.e., in Scheme I compounds (I), in Scheme II compounds (4) and (8) and the compounds of Formula XIII are prepared by alkylation of a substituted piperidine derivative of the formula

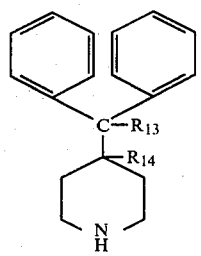

Formula XIV with an ω-haloalkyl substituted phenyl ketone of the formula

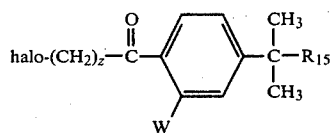

Formula XV wherein $R_{13}$ is hydrogen or hydroxy; $R_{14}$ is hydrogen; or $R_{13}$ and $R_{14}$ taken together form a second bond between the carbon atoms bearing $R_{13}$ and $R_{14}$; halo is a halogen atom, such as, chlorine, bromine or iodine; W is hydrogen or β-methoxyethoxymethyl-O (memoxy); z is an integer of from 1 to 5; $R_{15}$ is methyl or —COOalkyl wherein the alkyl moiety has from 1 to 6 carbon atoms and is straight or branched; with the provisos that when A is hydroxy, W is memoxy, and when $R_{15}$ is methyl, W is memoxy. When $R_{15}$ is —COOH the alkylation reaction is followed by base hydrolysis. When A is hydroxy in the ketone compounds (1), (4) or (8) the alkylation reaction is followed by cleavage of the memoxy group. The alkylation reaction is carried out in a suitable solvent preferably in the presence of a base and optionally in the presence of a catalytic amount of potassium iodide for about 4 to 120 hours and at temperatures of about 70° C. to the reflux temperature of the solvent. Suitable solvents for the alkylation reaction include alcohol solvents, such as, methanol, ethanol, isopropyl alcohol, or n-butanol; ketone solvents, such as, methyl isobutyl ketone; hydrocarbon solvents, such as, benzene, toluene or xylene; halogenated hydrocarbons, such as, chlorobenzene or methylene chloride or dimethylformamide. Suitable bases for the alkylation reaction include inorganic bases, for example, sodium bicarbonate, potassium carbonate, or potassium bicarbonate or organic bases, such as, a trialkylamine, for example, triethylamine or pyridine, or an excess of a compound of Formula XIV may be used. Cleavage of the β-methoxyethoxymethyl (MEM) group to give compounds (1), (4) or (8) wherein A is hydroxy is achieved by using trifluoroacetic acid at room temperature or using 5 to 8 equivalents of powdered anhydrous zinc bromide in methylene chloride at about 25° C. by the general procedure of E. J. Corey et al., Tetrahedron Letters No. 11, pp. 809–812 (1976). Base hydrolysis of the compounds wherein $R_{15}$ is —COOalkyl to give the corresponding compounds wherein $R_{15}$ is —COOH is achieved by treatment with an inorganic base, such as, sodium hydroxide in an aqueous lower alcohol solvent, such as, aqueous methanol, ethanol, isopropyl alcohol or n-butanol at reflux temperature for about ½ hour to 12 hours. When in compounds (8) A is hydroxy, removal of the MEM group using trifluoroacetic acid prior to base hydrolysis of the ester group is preferred.

The compounds of Formula XIV wherein each of $R_{13}$ and $R_{14}$ is hydrogen and wherein $R_{13}$ is hydroxy and $R_{14}$ is hydrogen are commercially available. The compounds of Formula XIV wherein $R_{13}$ and $R_{14}$ form a second bond between the carbon atoms beaing $R_{13}$ and $R_{14}$ may be prepared by dehydration of the corresponding compound wherein $R_{13}$ is hydroxy by procedures generally known in the art.

The compounds of general Formula XV wherein W is memoxy are prepared by treating a phenol of the following Formula XVI

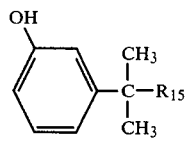

Formula XVI with an ω-halo alkanoic acid of the formula halo$(CH_2)_z$-COOH wherein halo is for example, chlorine or bromine and z is an integer of from 1 to 5 in the presence of boron trifluoride by the generally described procedure of Delschager and Mousa, Arch. Pharm. 306, 807 (1973). The phenol and acid are melted together at about 50° C. then cooled to about 10° C. after which boron trifluoride is added in an amount about 2.2 times the molar amount of phenol employed. The mixture is heated at about 70° C. for about 2 hours after which a 30% sodium acetate solution is added and extracted with ether. The organic layer is dried and the residue crystallized to give a hydroxy ketone of the formula

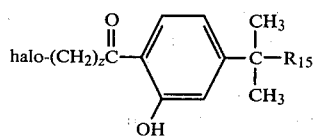

Formula XX wherein halo is, for example, chlorine or bromine, Z is 1 to 5 and $R_{15}$ is —$CH_3$ or —COOalkyl. The hydroxy ketone is then treated with a triethylammonium reagent of the formula $CH_3OCH_2CH_2OCH_2NEt_3^+Cl^-$ in acetonitrile according to the general procedure of E. J. Corey et al., Tetrahedron Letters No. 11, pp. 809–812 (1976).

The compounds of Formula XV wherein W is hydrogen are prepared by reacting an appropriate straight or branched lower alkyl $C_{1-6}$ ester of α,α-dimethylphenylacetic acid, which are known in the art or are prepared by procedures well known in the art, with a compound of Formula XVII, wherein halo and Z have the meanings defined above, under the general conditions of a Friedel-Crafts acylation. The reaction is carried out in a solvent such as, carbon disulfide, tetrachloroethane or nitrobenzene with carbon disulfide being a preferred solvent. The reaction time varies from about ½ hour to 8 hours, preferably 3 to 5 hours and the reaction temperature varies from about 0° to 25° C.

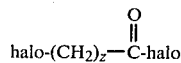

Formula XVII

The compounds of Formula XVII are commercially available or may be prepared by methods well known in the art. The compound of Formula XVI wherein $R_{15}$ is methyl is also commercially available (Aldrich). The compounds of Formula XVI wherein $R_{15}$ is —COOalkyl are prepared by treating a hot solution of an appropriate straight or branched alkyl $C_{1-6}$ ester of 3-trifluoroacetoxyphenylacetic acid in dimethoxyethane with a base, such as, sodium hydride under a nitrogen atmosphere followed by the addition of methyliodide in dimethoxyethane to the mixture over about a 20 minute period. The mixture is refluxed for about 3 hours then concentrated to remove most of the solvent after which diethyl ether, then water are added cautiously. The organic layer is separated, extracted with ether, dried over magnesium sulfate and distilled to give the appropriate ester of α,α-dimethyl-3-trifluoroacetoxyphenylacetic acid. To a solution of the methylated ester in 50% alcohol/water is added 3X molar amount of potassium carbonate. The solution is stirred at about 25° C. for about 8 hours then concentrated to a semisolid at reduced pressure at about 50° C., and upon cooling water is added and the mixture is neutralized with dilute hydrochloric acid then extracted with ether. The ether extract is dried over magnesium sulfate, filtered and concentrated to give the appropriate ester of 3-hydroxy-α,α-dimethylphenylacetic acid. The esters of trifluoroacetoxyphenylacetic acid are known in the art or may be prepared by procedures generally known in the art, for example, from m-hydroxyphenylacetic acid. For example, the hydroxyl group is protected by, e.g., treatment with trifluoroacetic anhydride, then the protected phenol acid may be treated with, e.g., an excess of an appropriate lower alcohol in the presence of a small amount of mineral acid, e.g., sulfuric acid at reflux.

EXAMPLE 1

α,α-Diphenyl-1-[4-[4-(hydroxy-tert-butyl)phenyl]-4-hydroxy-butyl]-4-piperidinemethanol A suspension of 2.15 g (0.0038 mole) of ethyl 4-[4-[4-(hydroxydiphenylmethyl)-1-piperidinyl]-1-hydroxybutyl]-α,α-dimethylbenzeneacetate in 50 ml of tetrahydrofuran was slowly added to a suspension of 0.7 g (0.0184 mole) of lithium aluminum hydride in 60 ml of tetrahydrofuran under a nitrogen atmosphere with stirring at such a rate to moderate the foaming. The mixture is stirred and heated at boiling for about 3 hours after which 30 ml of tetrahydrofuran is added. The mixture is refluxed for 4 hours and let stand overnight (about 16 hours). Stirring the mixture under a nitrogen atmosphere, 2 ml of water is added cautiously followed by 2 ml of 10% sodium hydroxide, 2 ml of water and 4 g of sodium sulfate. The mixture is warmed to 50°-55° C. and stirred for 45 minutes, filtered and the solid material is washed with tetrahydrofuran. The combined filtrates are evaporated in vacuo, and the residue is recrystallized from ethanol to give α,α-dipenyl-1-[4-[4-hydroxy-tert-butyl)phenyl]-4-hydroxybutyl]-4-piperidinemethanol, M.P. 134°–136° C.

EXAMPLE 2

Ethyl
4-[4-[4-(hydroxydiphenylmethyl)-1-piperidinyl]-1-hydroxybutyl]-α,α-dimethylbenzeneacetate hydrochloride A solution of 5.64 g (0.01 mole) of ethyl 4-[4-[4-(hydroxydiphenylmethyl)-1-piperidinyl]-1-oxobutyl]-α,α-dimethylbenzeneacetate hydrochloride in 200 ml of absolute ethanol and 50 ml of methanol and 0.5 g of platinum oxide is hydrogenated at about 50 psi for about 1 hour until the infrared showed no evidence of a ketone carbonyl function. The solution is filtered and the filtrate concentrated leaving a residue which is recrystallized from butanone and methanol-butanone to give ethyl 4-[4-[4-(hydroxydiphenylmethyl)-1-piperidinyl]-1-hydroxybutyl]-α,α-dimethylbenzeneacetate HCl, M.P. 185°–187° C.

EXAMPLE 3

4-[4-[4-(Hydroxydiphenylmethyl)-1-piperidinyl]-1-hydroxybutyl]-α,α-dimethylbenzeneacetic acid To a solution of 0.6 g of ethyl 4-[4-[4-(hydroxydiphenylmethyl)-1-piperidinyl]-1-hydroxybutyl]-α,α-dimethylbenzeneacetate in 20 ml of absolute ethanol is added 10 ml of a 50% solution of sodium hydroxide. The mixture is refluxed for 3½ hours and concentrated to a solid after which a minimum amount of methanol to dissolve the residue is added. 10% Aqueous HCl is added until pH 7 is reached, the methanol removed by evaporation and water (25 ml) is added. The resulting precipitate is recrystallized from methanol-butanone to give 4-[4-[4-(hydroxydiphenylmethyl)-1-piperidinyl]-1-hydroxybutyl]-α,α-dimethylbenzeneacetic acid, M.P. 195°–197° C.

EXAMPLE 4

α,α-Diphenyl-1-[4-(4-tert-butyl-3-hydroxyphenyl)-4-hydroxybutyl]-4-piperidinemethanol A mixture of 0.1 mole of 4'-tert-butyl-4-[4-(hydroxydiphenylmethyl)piperidinyl]butyrophenone in 30 ml of trifluoroacetic anhydride is stirred for 4 hours at 0° C., concentrated to a solid, then reduced catalytically in a Paar apparatus usng platinum oxide in 20 ml of methanol until an equivalent amount of hydrogen is taken up to give α-(p-tert-butylphenyl)-4-(α-trifluoroacetoxy-α-phenylbenzy)-1-piperidinebutanol which is treated with a slight excess of thallium trifluoroacetate in 50 ml of trifluoroacetic acid at 72° C. for 3 hours after which 1 equivalent of lead tetra-acetate in 10 ml of trifluoroacetic acid is added. The mixture is stirred for 30 minutes then 1 equivalent of triphenylphosphine is added. Stirring is continued for 30 minutes then the excess solvent is removed at reduced pressure. Cold and dilute (6N) hydrochloric acid (15 ml) is added and the mixture is filtered. The filtrate is made basic using 10% aqueous sodium hydroxide and a minimum amount of ethanol is added to bring about complete solution. The solution is refluxed 4 hours, neutralized with dilute HCl, concentrated, extracted with toluene, dried, filtered and concentrated to give α,α-diphenyl-1-[4-(4-tert-butyl-3-hydroxyphenyl)-4 -hydroxy]butyl-4-piperidinemethanol.

EXAMPLE 5

Ethyl 4-[4-[4-(hydroxydiphenylmethyl)-1-piperidinyl]-1-hydoxybutyl]-α,α-dimethyl-3-hydroxybenzeneacetate (A) To 700 ml of carbon disulfide containing 36.5 g (0.254 mole) of 4-chlorobutyryl chloride is added 74.5 g (0.56 mole) of aluminum chloride with stirring at −10° C. Stirring is continued for about 15 minutes at about 25° C. then the mixture is recooled to 5° C. and 48.4 g (0.294 mole) of ethyl α,α-dimethylphenylacetate in 100 ml of carbon disulfide is added. The reaction mixture is stirred on an ice bath for 3½ hours then stirred to 15½ hours at 25° C. then poured into HCl-ice water and extracted with chloroform. The extract is washed with dilute sodium carbonate solution, water and saturated sodium chloride solution, dried over magnesium sulfate, and evaporated giving as a solid ethyl 4-(4-chloro-1-oxobutyl)-α, α-dimethylphenylacetate.

(B) A mixture of 4.5 g (0.0163 mole) of α,α-diphenyl-4-piperidinemethanol, 6.1 g (0.0205 mole) of ethyl 4-(4l-chloro-1-oxobutyl)-α,α-dimethylphenylacetate, 5 g (0.05 mole) of potassium bicarbonate and 0.05 g of potassium iodide in 50 ml of toluene is stirred and refluxed for 72 hours then filtered. Ether then ethereal hydrogen chloride is added to the filtrate, and the resulting precipitate collected and recrystalized several times from methanol-butanone and butanone to give ethyl 4-[4-[4-(hydroxydiphenylmethyl)-1-piperidinyl]-1-oxobutyl]-α,α-dimethylbenzeneacetate hydrochloride. M.P. 205.5°–208° C.

(C) When in the procedure of Example 4 an appropriate amount of ethyl 4-[4-[4-(hydroxydiphenylmethyl)-1-piperidinyl]-1-oxobutyl]-α,α-dimethylbenzeneacetate, prepared from the hydrochloride salt obtained in (B) above, is substituted for 4'-tert-butyl-4-[4-(hydroxydiphenylmethyl)piperidinyl]butyrophenone, ethyl 4-[4-[4-(hydroxydiphenylmethyl)-1-piperidinyl]-1-hydroxybutyl]-α,α-dimethyl-3-hydroxybenzene acetate is obtained.

EXAMPLE 6

α,α-Diphenyl-1-[4-(4-tert-butyl-2-hydroxyphenyl)-4-hydroxybutyl]-4-piperidinemethanol A solutin of 0.10 mole of 3-tert-butylphenol in 0.20 mole of ω-chlorobutyric acid is heated in a pressure vessel at 50° C. for about 1 hour then cooled to 10° C. after which 0.35 mole of boron tirfluoride is added. The mixture is heated to about 70° C. for about 2 hours and cooled, after which 200 ml of a 30% solution of sodium acetate is added followed by extraction with ether to give 4'-tert-butyl-2'-hydroxy-4-chlorobutyrophenone. The phenone is treated with a 10% excess of β-methoxyethoxymethyl triethylammonium chloride $(CH_3OCH_2CH_2OCH_2N(C_2H_5)_3{}^+Cl^-)$ in 250 ml of dry acetonitrile with stirring for 18 hours at about 25° C. The precipitated triethylamine hydrochloride is filtered, and the filtrate concentrated to a semi-solid which is dissolved in dry ether. Residual amounts of triethylamine are removed by filtration. Concentration of the ether solution gives 4'-tert-butyl-2'-memoxy-4-chlorobutyrophenone.

When in the procedure of Example 5(B) an appropriate amount of 4'-tert-butyl-4-chloro-2'-memoxybutyrophenone is substituted for ethyl 4-(4-chloro-1-oxobutyl)-α,α-dimethylphenylacetate, 4'-tert-butyl-2'-memoxy-4-[4-(hydroxydiphenylmethyl)-1-piperidinyl]- butyrophenone is obtained, and upon treatment of 1 equivalent of said butyrophenone with trifluoroacetic acid, concentrating and neutralizing, 4'-tert-butyl-2'-hydroxy-4-[4-(hydroxydiphenylmethyl)-1-piperidinyl]-butyrophenone is obtained.

When in the procedure of Example 2 an appropriate amount of 4'-tert-butyl-2'-hydroxy-4-[4-(hydroxydiphenylmethyl)-1-piperidinyl]butyrophenone hydrochloride, prepared from the free base obtained above, is substituted for 4-[4-[4-(hydroxydiphenylmethyl)-1-piperidinyl]-1-oxobutyl]-α,α-dimethylbenzene acetate, α,α-diphenyl-1-(4-(4-tert-butyl-2-hydroxy)phenyl)-4-hydroxybutyl-4-piperidinemethanol hydrochloride is obtained.

EXAMPLE 7

Ethyl 4-[3-[4-(hydroxydiphenylmethyl)-1-piperidinyl]-1-hydroxypropyl]-α,α-dimethylbenzeneacetate When in the procedure of Example 5(A), an appropriate amount of 3-chloropropionyl chloride is substituted for 4-chlorobutyryl chloride, ethyl 4-(3-chloro-1-oxopropyl)-α,α-dimethylphenylacetate is obtained.

When in the procedure of Example 5(B) an appropriate amount of 4-(diphenylmethylene) piperidine is substituted for 4-(α,α-diphenyl)piperidinemethanol, and an appropriate amount of ethyl 4-(3-chloro-1-oxopropyl)-α,α-dimethylphenylacetate is substituted for ethyl 4-(4-chloro-1-oxobutyl)-α,α-dimethylphenylacetate, ethyl 4-[3-(4-(diphenylmethylene)-1-piperidinyl]-1-oxopropyl]-α,α-dimethylbenzene acetate hydrochloride is obtained.

When in the procedure of Example 2 an appropriate amount of ethyl 4-[3-[4-(diphenylmethylene)-1-piperidinyl]-1-oxopropyl]-α,α-dimethylbenzene acetate hydrochloride is substituted for ethyl 4-[4-[4-(hydroxydiphenylmethyl)-1-piperidinyl]-1-oxobutyl]-α,α-dimethylbenzeneacetate hydrochloride, ethyl 4-[3-[4-(hydroxydiphenylmethyl)-1-piperidinyl]-1-hydroxypropyl]-α,α-dimethylbenzeneacetate hydrochloride is obtained.

EXAMPLE 8

4-[4-[4-(hydroxydiphenylmethyl)-1-piperidinyl]-1-hydroxybutyl]-α,α-dimethyl-3-hydroxybenzeneacetic acid A hot solution of 1 equivalent of ethyl 3-trifluoroacetoxyphenylacetate in dimethoxyethane is treated with 2.1 equivalents in sodium hydride under a nitrogen atmosphere followed by the addition of 2.1 equivalents of methyliodide in dimethoxyethane over about a 20 minute period. The mixture is refluxed for about 3 hours then concentrated to remove most of the solvent after which diethyl ether, then water are added cautiously. The organic layer is separated, extracted with ether, dried over magnesium sulfate, and distilled to give ethyl α,α-dimethyl-3-trifluoroacetoxyphenylacetate. To a solution of the methylated ester in 50% alcohol/water is added 3X molar amount of potassium carbonate. The solution is stirred at 25° C. for 8 hours then concentrated to a semisolid at reduced pressure at 50° C. Upon cooling water is added and the mixture is neutralized with dilute hydrochloric acid then extracted with ether. The ether extract is dried over magnesium sulfate, filtered and concentrated to give ethyl α,α-dimethyl-3-hydroxyphenylacetate.

When in the procedure of Example 4(A) an appropriate amount of ethyl α,α-dimethyl-3-hydroxyphenylacetate is substituted for 3-tert-butylphenol, ethyl 4-(4-chlorobutyryl)-3-memoxy-α,α-dimethylphenylacetate is obtained.

When in the procedure of Example 5(B) an appropriate amount of ethyl 4-(4-chlorobutyryl-3-memoxy-α,α-dimethylphenylacetate is substituted for ethyl 4-(4-chloro-1-oxobutyl)-α,α-dimethylphenylacetate, ethyl 4-[4-[4-(hydroxydiphenylmethyl)-1-piperidinyl]-1-oxobutyl]-α,α-dimethyl-3-memoxybenzeneacetate is obtained. One equivalent of the memoxy acetate is treated with trifluoroacetic acid. The resulting solution is concentrated to a solid, triturated with sodium bicarbonate solution, extracted into methylene chloride, washed with water and saturated sodium chloride, dried over magnesium sulfate, filtered and concentrated to give ethyl 4-[4-[4-(hydroxydiphenylmethyl)-1-piperidinyl]-1-oxobutyl]-α,α-dimethyl-3-hydroxybenzeneacetate.

When in the procedure of Example 2 an appropriate amount of ethyl 4-[4-[4-(hydroxydiphenylmethyl)-1-piperidinyl]-1-oxobutyl]-α,α-dimethyl-(3-hydroxybenzene)-acetate hydrochloride is substituted for ethyl 4-[4-[4-(hydroxydiphenylmethyl)-1-piperidinyl]-1oxobutyl]-α,α-dimethylbenzeneacetae hydrochloride, the compound ethyl 4-[4-[4-(hydroxydiphenylmethyl)-1-piperidinyl]-1-hydroxybutyl]-α,α-dimethyl-(3-hydroxybenzene)acetate is obtained, and when an appropriate amount of said last named compound is substituted for ethyl 4-[4-[4-(hydroxydiphenylmethyl)-1-piperidinyl]-1-hydroxybutyl]-α,α-dimethylbenzeneacetate in the procedure of Example 3, 4-[4-[4-(hydroxydiphenylmethyl)-1-piperidinyl]-1-hydroxybutyl]-α,α-dimethyl-3-hydroxybenzeneacetic acid is obtained.

EXAMPLE 9

An illustrative composition for hard gelatin capsules is as follows:

| (a) | α,α-diphenyl-1-[4-[4-(hydroxy-tert-butyl)phenyl]-4-hydroxybutyl]-4-piperidinemethanol | 10 mg |
|---|---|---|
| (b) | talc | 5 mg |
| (c) | lactose | 100 mg |

The formulation is prepared by passing the dry powders of (a) and (b) through a fine mesh screen and mixing them well. The powder is then filled into hard gelatin capsules at a net fill of 115 mg per capsule.

EXAMPLE 10

An illustrative composition for tablets is as follows:

| (a) | Ethyl 4-[4-[4-(hydroxydiphenylmethyl)-1-piperidinyl]-1-hydroxybutyl]-α,α-dimethylbenzeneacetate | 5 mg |
|---|---|---|
| (b) | starch | 43 mg |
| (c) | lactose | 60 mg |
| (d) | magnesium stearate | 2 mg |

The granulation obtained upon mixing the lactose with the compound (a) and part of the starch and granulated with starch paste is dried, screened, and mixed with the magnesium stearate. The mixture is compressed into tablets weighing 110 mg each.

EXAMPLE 11

An illustrative composition for an aerosol solution is the following:

| | | Weight percent |
|---|---|---|
| (a) | α,α-diphenyl-1-[4-[4-(hydroxy-tert-butyl)phenyl]-4-hydroxybutyl]-4-piperidinemethanol | 5.0 |
| (b) | ethanol | 35.0 |
| (c) | propane | 60.0 | ps The materials (a), (b) and (c) are packaged in 15 ml stainless steel containers equipped with a metering valve designed to meter 0.2 grams per dose, an equivalent of 10 mg of novel compound (a).

EXAMPLE 12

An illustrative composition for an aerosol suspension is the following:

| | | Weight percent |
|---|---|---|
| (a) | 4-[4-[4-(hydroxydiphenylmethyl)-1-hydroxybutyl]-α,α-dimethylbenzeneacetic acid (Particle size <10μ) | 20.0 |
| (b) | sorbitan trioleate | 0.5 |
| (c) | isobutane | 79.5 |

The materials (a)–(c) are packaged in 15 ml stainless steel containers equipped with a metering valve designed to meter 50 mg per dose, an equivalent of 10 mg of novel compound (a).

EXAMPLE 13

An illustrative composition for an injectable suspension is the following 1 ml ampul for an intramuscular injection.

| | | Weight percent |
|---|---|---|
| (a) | α,α-diphenyl-1-[4-[4-(hydroxy-tert-butyl)phenyl]-4-hydroxybutyl]-4-piperidinemethanol (particle size <10μ) | 1.0 |
| (b) | polyvinylpyrrolidone (M.W. 25000) | 0.5 |
| (c) | lecithin | 0.25 |
| (d) | water for injection to make | 100.0 |

The materials (a)–(d) are mixed, homogenized, and filled into 1 ampuls which are sealed and autoclaved 20 minutes at 121° C. Each ampul contains 10 mg per ml of novel compound (a).

We claim:

1. A compound of the formula

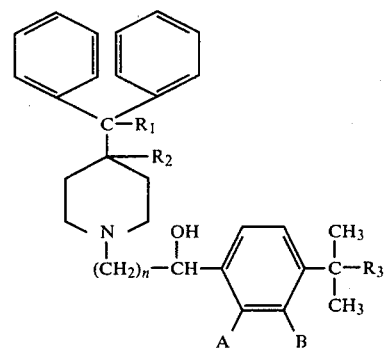

wherein $R_1$ represents hydrogen or hydroxy; $R_2$ represents hydrogen; or $R_1$ and $R_2$ taken together form a second bond between the carbon atoms bearing $R_1$ and $R_2$; n is an integer of from 1 to 5; $R_3$ is —COOH or —COOalkyl wherein the alkyl moiety has from 1 to 6 carbon atoms and is straight or branched; each of A and B is hydrogen or hydroxy; with the proviso that at least one of A or B is hydrogen; and pharmaceutically acceptable salts and individual optical isomers thereof.

2. A compound of claim 1 wherein $R_1$ is hydrogen or $R_1$ and $R_2$ taken together form a second bond between the carbon atoms bearing $R_1$ and $R_2$.

3. A compound of claim 2 wherein n is 3 or 4.

4. A compound of claim 2 wherein $R_3$ is —COOalkyl.

5. A compound of claim 2 wherein $R_3$ is —COOH.

6. A compound of claim 1 of the formula

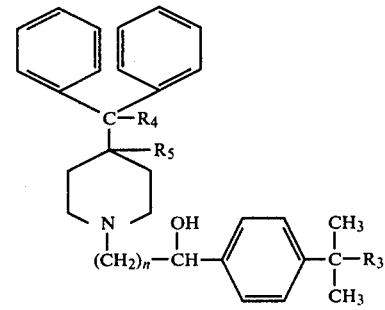

wherein $R_4$ is hydroxy and $R_5$ is hydrogen, or $R_4$ and $R_5$ taken together form a second bond between the carbon atoms bearing $R_4$ and $R_5$; n is the integer 3; and $R_3$ is —COOH or a pharmaceutically acceptable salt thereof.

7. A compound of claim 1 which is ethyl 4-[4-[4-(hydroxydiphenylmethyl)-1-piperidinyl]-1-hydroxybutyl]-α,α-dimethylbenzene acetate or a pharmaceutically acceptable salt thereof.

8. A compound of claim 1 which is 4-[4-[-4-(hydroxydiphenylmethyl)-1-piperidinyl]-1-hydroxybutyl]-α,α-dimethylbenzeneacetic acid or a pharmaceutically acceptable salt thereof.

9. A compound of claim 1 which is 4-[4-[4-(hydroxydiphenylmethyl)-1-piperidinyl]-1-hydroxybutyl]-α,α-dimethyl-(3-hydroxybenzene)acetic acid or a pharmaceutically acceptable salt thereof.

10. A pharmaceutical composition in unit dosage form comprising an effective antiallergic amount of a compound of claim 1 and a significant amount of a pharmaceutically acceptable carrier.

11. A method of treating allergic reactions in a patient in need thereof which comprises administering to said patient an effective amount of a compound of claim 1.

* * * * *

UNITED STATES PATENT AND TRADEMARK OFFICE

CERTIFICATE EXTENDING PATENT TERM
UNDER 35 U.S.C. § 156

PATENT NO.     :   4,254,129

ISSUED         :   March 3, 1981

INVENTOR(S)    :   Albert A. Carr et al.

PATENT OWNER   :   Merrell Pharmaceuticals

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 679 days from April 10, 1999, the original expiration date of the patent, with all rights pertaining thereto as provided by 35 U.S.C. § 156(b).

I have caused the seal of the Patent and Trademark Office to be affixed this 15th day of July 1998.

Bruce A. Lehman
Assistant Secretary of Commerce and
   Commissioner of Patents and Trademarks